United States Patent [19]

Turner et al.

[11] Patent Number: 5,149,824
[45] Date of Patent: Sep. 22, 1992

[54] PROCESS FOR PREPARING ARYLAMIDE BISNADIMIDES

[75] Inventors: S. Richard Turner; Robert J. Perry, both of Pittsford; Richard W. Blevins, Rochester, all of N.Y.

[73] Assignee: Eastman Kodak Company, Rochester, N.Y.

[21] Appl. No.: 724,269

[22] Filed: Jul. 1, 1991

[51] Int. Cl.$^5$ .............................................. C07D 209/56
[52] U.S. Cl. ................................... 548/435; 546/167; 546/272
[58] Field of Search ................ 548/435; 546/167, 272; 564/132, 152

[56] References Cited

U.S. PATENT DOCUMENTS 4,239,883 12/1980 Stenzenberger ..................... 548/435
4,861,885 8/1989 Kramer et al. ....................... 564/152

OTHER PUBLICATIONS

Hoyt et al., ACS Symp. Ser. 435 (Liq.-Cryst. Polymers), pp. 190-206 (1990).
Mar., Advanced Organic Chemistry, pp. 574-575, John Wiley & Sons 1985.

Primary Examiner—Joseph Paul Brust
Assistant Examiner—MarySusan H. Gabilan
Attorney, Agent, or Firm—J. Jeffrey Hawley

[57] ABSTRACT

There is provided a method for the production of an arylamide bisnadimide. The arylamide bisnadimide is useful as a prepolymer. The method includes the step of: condensing a nadimide compound having the nitrogen of said nadimide substituted with a halogen substituted aromatic group, with a dinucleophile in the presence of carbon monoxide, a base and a palladium catalyst.

10 Claims, No Drawings

PROCESS FOR PREPARING ARYLAMIDE BISNADIMIDES

FIELD OF THE INVENTION

The present invention is directed to the preparation of useful polymer precursors. These precursors are useful in the preparation of addition polyimide polymers with high thermal stability.

BACKGROUND OF THE INVENTION

There is a continuing need for high performance thermoset polymers. The properties that are usually important are high service use temperatures, better physical properties and low moisture uptake.

Epoxy resins fall short of performance requirements for advanced composites because of their insufficient thermal stability and high moisture uptake. This is probably due to the large number of hydroxy groups in these polymers.

One alternative to epoxies is a class of polymers that is referred to as polyimides. However, these polymers are often difficult to use due to their limited solubility and their limited thermal processability. Most fully cyclized polyimides are either insoluble or soluble only in high boiling solvents such as N-methylpyrrolidinone and the like. Most polyimides decompose before they melt and thus, can not be melt processed.

Another alternative is a class of polymers known as addition polyimides. Polymers have been developed based on bismaleimides and bisnadimides as shown, for example, in U.S. Pat. No. 4,239,883 to Stenzenberger. These polymers are made by first preparing the bismaleimide or bisnadimide prepolymer and then heating the prepolymer to a temperature between about 100° to 400° C. These prepolymers are thought to react by free radical addition polymerization of the unsaturated bonds on the bismaleimide or bisnadimide at the elevated temperatures.

There are several different chemical linkages that can be used to join the reactive maleimide or nadimide ends. One of the most important connections has been through arylamide chains because of the excellent thermal stability of these chains. Addition polyimides having these connecting chains are commercially available.

While these addition polyimides have many desirable properties, they have been difficult to make. The conventional synthesis of these materials involves the reaction of a diamine with maleic anhydride or nadic anhydride followed by cyclization of the resultant adduct with heat or chemical reagents. This process is illustrated with nadic anhydride as follows:

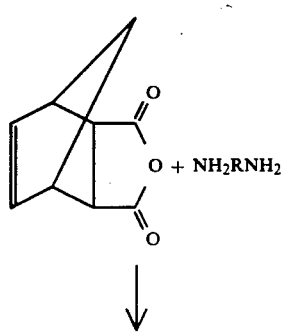

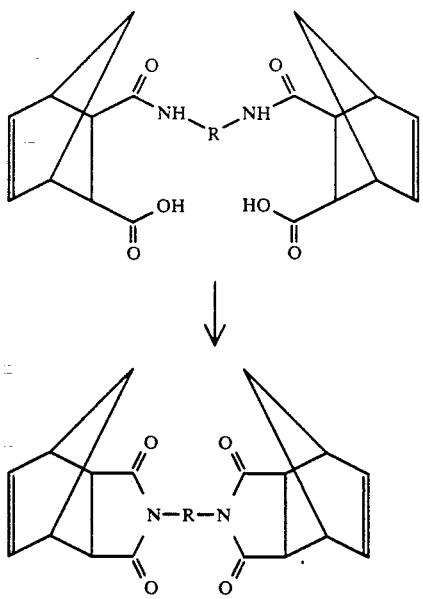

For the preparation of arylamide derived materials (where R contains an aromatic amide group), the use of moisture sensitive acid chlorides have been needed to obtain the amide linkages. In many cases the reduction of aromatic nitro groups to aromatic amines have been employed as a reaction step. These reduction reactions are generally not complete and require several recrystallizations in order to obtain bifunctional bismaleimides or bisnadimides of sufficient purity for effective network formation.

In all of these processes, there is a final cyclization step. Without the cyclization step, the end nadimide group is not sufficiently active. Nonreactive end groups could lead to less than optimal performance in the final cured composite structure. Thus, there is a continuing need for improved processes for making addition polyimide polymers. It would be desirable if the process could avoid the use of acid chloride reactions, nitro reductions, and incomplete cyclization.

SUMMARY OF THE INVENTION

In accordance with the present invention, there is provided a method for the production of an arylamide bisnadimide, said method comprising the step of: condensing a nadimide compound having the nitrogen of said nadimide substituted with a halogen substituted aromatic group, with a dinucleophile in the presence of carbon monoxide, a base and a palladium catalyst.

DETAILED DESCRIPTION OF THE INVENTION

In accordance with the present process, a nadimide compound, wherein the nitrogen of said nadimide is substituted with a halogen substituted aromatic group is condensed with a dinucleophile. The reaction can be illustrated by the following where the dinucleophile is a primary diamine and X is a halogen, preferably iodine:

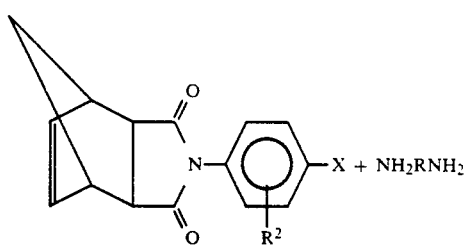

↓ CO Base | Pd

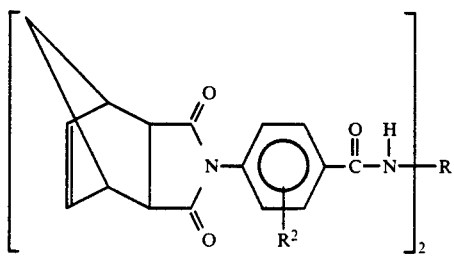

The nadimide compounds having the nitrogen of said nadimide substituted with a halogen substituted aromatic are known compounds that are made by conventional methods. The compounds are prepared for example, by the reaction of a halogen substituted aromatic primary amine compound with nadic anhydride, followed by cyclization with acetic anhydride and sodium acetate. Reference is made to Agustin, M.; Koehler, M.; Haertling S.; J. Prakt Chem (1973) 315(4) 717.

This aromatic group can be further substituted with other groups, $R^2$, such as: alkyl, alkoxy, aryloxy (wherein the alkyl group preferably has from 1 to 22 carbon atoms and the aryl group has from 6 to 10 carbon atoms), disubstituted amino, cyano, chloro, aryl, acetyl, nitro, carboxylic acid (and derivatives such as esters), sulfone and amide. There can be up to four $R^2$ groups on the rings (including the amine group). Other useful aromatic halides include compounds having one or more heteroatoms in the ring structure. Thus, the halogen substituted aromatic group can be any aromatic or heteroaromatic group having up to four aromatic rings. The unconnected bond is a former amine group that provides the nitrogen in the nadimide (formed by reaction with nadic anhydride). Useful groups include (X represents halogen):

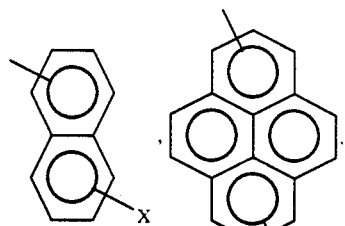

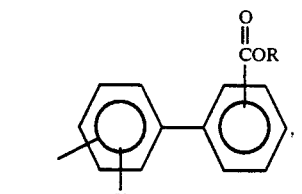

-continued

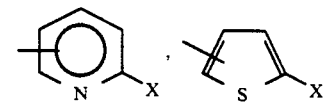

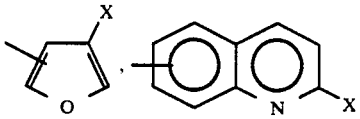

The preferred aromatic group is aryl, the preferred halogen is iodine and therefore the preferred halogen substituted aromatic group is derived from p- or m-iodoaniline. Consequently, the preferred nadimide is N-(4-iodophenylnadimide).

The described aromatic substituted nadimide is condensed with a dinucleophile in the presence of carbon monoxide, a base and a palladium catalyst. A wide variety of dinucloephiles are useful. Primary diamines are preferred. These diamines are known compounds. Useful diamines are disclosed in columns 9 and 10 of the Stenzenberger U.S. Pat. No. 4,239,883 cited above. Particularly preferred diamines are those having the formula H2NRNH2 wherein R contains at least one aromatic group.

The currently preferred R groups, since they provide for bisnadimide prepolymers with desirable properties, have the structural formulae:

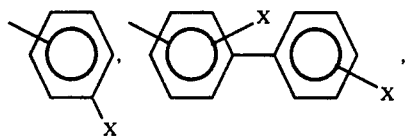

(Example 1)

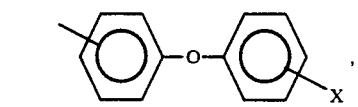

(Ex. 3)

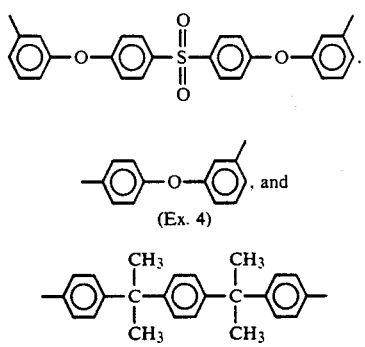

Dinucleophiles, other than primary diamines, can also be used. Useful dinucleophiles include bisphenols and bisthiophenols.

As can be seen by the above description, a wide variety of nadimide compounds having the nitrogen of the nadimide substituted with a halogen substituted aromatic group and dinucleophile reactants can be used in the processes of this invention. Preferably, such reactants are "stable" under the reaction conditions employed, i.e., they do not decompose to an unacceptable extent during the process of this invention. The organic materials used in this invention are also "suitably reactive", i.e., they react in the process of this invention without entering into an unacceptable amount of undesirable side reaction(s). Thirdly, the organic reactants used in this invention should be "sterically suitable", i.e., they should not be so bulky as to unduly retard the reaction by steric hindrance. Examples of such reactants have been given above.

The nadimide compound having the nitrogen of said nadimide substituted with a halogen substituted aromatic group and dinucleophile reactants are contacted with carbon monoxide. The CO may be at atmospheric pressure or at a higher pressure. Carbon monoxide pressures in the range of from about 1 to about 200 atmospheres or higher can be used in the process.

Pressures lower than atmospheric can be used if desired, but generally do not confer any advantage.

It is convenient to add an excess of carbon monoxide to the reaction zone. The excess of CO need not be measured; one may merely pressurize the vessel with CO to the desired reaction pressure.

When one of the organic reactants is used in excess, it is preferably used in an amount of from 1.001 to about 5 times the molar amount required by stoichiometry.

The process of this invention is conducted in the presence of a liquid reaction medium to facilitate contact of the reactants. A variety of organic compounds can be used for this purpose as long as the reaction medium is "inert", i.e., does not enter into the reaction in an undesired way. It is preferred that the reaction medium dissolve the reactants to an appreciable extent. A preferred solvent of this type is tetrahydrofuran or diglyme (2-methoxyethyl ether), or glyme (1,2-dimethoxyethane). A dipolar aprotic solvent is preferentially employed. Such solvents lack acidic, easily abstractable hydrogens and are highly polar. Typical dipolar aprotic solvents are dimethylformamide, N,N-dimethylacetamide, N-methylpyrrolidinone, dimethylsulfoxide, hexamethylphosphoramide, N-cyclohexyl-pyrrolidinone, dimethylimidazolidinone and the like. The amount of liquid reaction medium is not critical. Generally, one uses enough medium to facilitate the reaction. There is no theoretical upper limit on the amount of reaction medium employed. However, practical limits are imposed by the size of the reaction vessel, the ease of separation of product(s) from the reaction medium, cost, and similar considerations. Generally, the amount of liquid reaction medium employed is within the range of from about 0.1 to about 800 parts based on the weights of haloaromatic employed.

The process of this invention is conducted in the presence of a catalyst. The catalyst is preferentially a palladium compound, where palladium is present in the zero valent or divalent state. The palladium catalysts generally have one or more ligands attached to the palladium by ionic or covalent bonds. Simple palladium salts such as $PdX'_2$ wherein $X'$ is Cl, Br or I can be used. Other representative palladium catalysts are listed in Table 1 below:

TABLE 1

| Palladium Catalysts | |
|---|---|
| $Pd^{+2}$ | |
| $PdX_2$ | X = Cl, Br, I |
| $PdX_2L_2$ | X = Cl, Br, I |
| | L = $R_3P$, where R = alkyl or aryl |
| $Pd(OAc)_2$ | OAc = acetate |
| $Pd(OAc)_2L_2$ | OAc = acetate |
| $PdCl_2(RCN)_2$ | R = $CH_3$, Phenyl |
| $PhPdXL_2$ | X = Br, I |
| $PdCl_2(COD)_2$ | COD = cis,cis-1,5-cyclooctadiene and; |
| $Pd(acac)_2$ | acac = 2,4-pentanedionate |
| $PdCl_2(DPPE)$ | |
| $PdCl_2(DPPP)$ | |
| $PdCl_2(DPPF)$ | |
| $Pd^{(0)}$ | |
| PdL | L = $R_3P$ where R = alkyl or aryl and; |

$$Pd_2\left[ Ph \diagup\!\!\!\diagdown \overset{O}{\underset{\|}{C}} \diagup\!\!\!\diagdown Ph \right]_3$$

$Pd(DPPE)_2$
$Pd(DPPP)_2$
$PD(DPPB)_2$
(In the formulae above:
DPPE = 1,2-bis(diphenylphosphino)ethane
DPPP = 1,3-bis(diphenylphosphino)propane
DPPF = 1,1-bis(diphenylphosphino)ferrocene
DPPB = 1,4-bis(diphenylphosphino)butane)

A catalytic amount of catalyst is employed. By "catalytic amount" is meant an amount of catalyst which catalyzes the reaction to the desired extent. Generally, the amount of catalyst is about 0.002 mole percent based on the amount of nadimide compound. There is no theoretical upper limit on the amount of catalyst, this being defined by secondary considerations such as cost and ease of separation of the catalyst from products. A preferred catalytic amount is from about 0.005 to about 0.20 moles per mole of aromatic halide, more preferably from about 0.02 to about 0.10 mole per mole of halide reactant.

The reaction can take place in the presence of an activation ligand such as phosphine or arsine. Such a ligand may be used with a catalyst, for example, triphenylphosphine with bis(triphenylphosphine)palladium(II) chloride, to increase the rate of the catalyzed reaction. The amount of ligand used is desirably between about 0.01 mole and about 5.0 moles per mole of metal catalyst, and more desirably at about 2.0 moles per mole of metal catalyst. It is believed that the presence of the activating ligand speeds up the oxidative addition of such catalysts to the aromatic halide reactant by making the catalyst more nucleophilic.

The process of this invention is preferably conducted in the presence of a base to neutralize the by-product hydrogen halide. The base may be a tertiary amine such as tributylamine, 2,6-lutidine, 1,8-diazabicyclo[5.4.0]undec-7-ene (DBU), 1,5-diazabicyclo[4.3.0]non-5-ene (DBN) or have the formula:

NR₃ wherein each R is independently selected from lower alkyl groups having from about 2 to about 6 carbon atoms. The base may be immobilized on a crosslinked polymer such as poly(vinylpyridine) beads. Alternatively, the base may be another type of basic substance which does not react with the reactants, e.g., a metal carbonate such as $K_2CO_3$ or a metal hydroxide such as $Ca(OH)_2$. Generally, one employs at least enough base to react with the by-product HX produced. An excess can be used, if desired. As with the reactants, solvents and catalysts, a skilled practitioner will recognize that the exact structure of the base is not critical, and the examples of compounds set forth above are merely illustrative and not limiting examples of materials that can be used in this invention. A skilled practitioner will recognize that other materials can be substituted in this invention to achieve similar results.

The process of this invention is preferably conducted at a temperature within the range of from about ambient to about 250° C. A preferred temperature range is from about 60° C. to about 160° C. A skilled practitioner will recognize that the reaction temperature is not critical, and that temperatures outside this range can be employed, if desired. Generally, one selects a reaction temperature which affords a reasonable rate of reaction and which does not give an undue amount of decomposition of products or reactants. The reaction time is not a truly independent variable, but is dependent to some extent on other reaction parameters such as reactivity of the reactants, amount and activity of catalyst, reaction temperature, pressure, and similar variables. Generally speaking, reaction times within the range of from about 0.1 to about 100 hours are used.

The following examples are presented for a further understanding of the invention.

EXAMPLES

Preparation of p-iodo-N-phenylmaleimide:

The title compound was prepared by standard maleimide procedures involving the reaction of p-iodoaniline with maleic anhydride and then subsequent cyclization with acetic anhydride and sodium acetate.

Preparation of o-iodo-N-phenylnadimide

The title compound was prepared as follows: 52.8 g (0.176 mol) of the iodomaleimide prepared as described above was dissolved in 160 mL of dry tetrahydrofuran. 15 g (0.217 mol) of freshly cracked cyclopentadiene were added. The reaction was cooled in dry ice and after one hour, a white precipitate was isolated by filtration. This material was crystallized from 95% ethanol to yield 55 g (86%) of white needles which had a melting point of 186° C. The NMR and IR spectra along with the elemental analysis were consistent with the title structure.

EXAMPLE 1: CONDENSATION OF P-IODO-N-PHENYLNADIMIDE WITH 4,4-OXYDIANILINE

A clean reaction bottle was charged in a dry box with 7.3 g (0.02 mol) of the iodonadimide prepared as described above, 2.00 g (0.01 mol) of oxydianiline 47 g of N,N-dimethylacetamide, 0.314 g of triphenylphosphine (6 mol% based on the iodonadimide), 0.421 g bis(triphenylphosphine)palladium(II) chloride (3 mol% based on the iodonadimide) and 3.65 g of 1,8-diazabicyclo[5.4.0]undec-7-ene (120 mol%). The reaction vessel was purged with carbon monoxide and then brought to a pressure of about 8 Kg/cm² in an oil bath. After one hour, a gas chromatograph analysis of the reaction mixture indicated that all of the oxydianiline had been consumed. The remaining carbon monoxide pressure was released, the reaction mixture was poured into ethyl alcohol and the solids collected by filtration. A crude product of 7.0 g (100%) was obtained. Proton NMR in dimethylsulfoxide showed resonances consistent with the following structure:

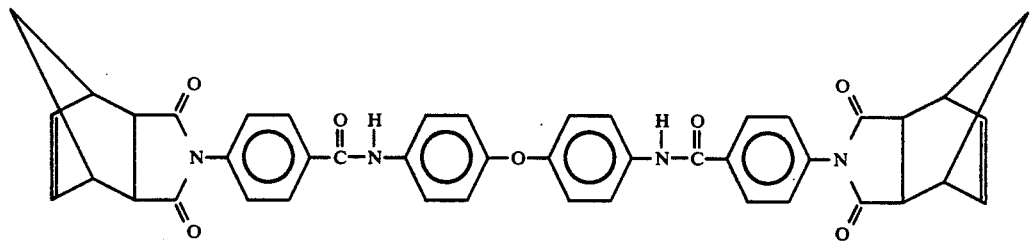

10.2(s) NH(2H), 7.85 (quartet) ArH (8H), 7.15 (quartet) ArH (8H), 6.2(s) vinyl H (4H), 3.5(s) CH(4H), 1.6(s) CH (4H).

EXAMPLE 2: CONDENSATION OF P-IODO-N-PHENYLNADIMIDE WITH 5-AMINO-3-(4-AMINOPHENYL)-1,1,3-TRIMETHYLINDAN

The procedure described in example 1 was repeated with the following reagents and solvent:

| | | |
|---|---|---|
| 5-amino-3-(4-aminophenyl)-1,1,3-trimethylindan | 1.09 g | 4.11 mmole |
| p-iodo-N-phenylnadimide | 3.0 g | 8.22 mmole |
| bis(triphenylphosphine) palladium(II) chloride | 0.173 g | 0.25 mmole |
| N,N-dimethylacetamide | 15 g | |
| 1,8-diazabicyclo[5.4.0] undec-7-ene | 1.50 g | 9.85 mmole |
| triphenylphosphine | 0.129 g | 0.49 mmole |

The proposed structure was the same as that for example 1 except for the divalent phenylindan group in place of the divalent oxydianiline group. The NMR sprctrum was consistant with the proposed structure.

EXAMPLE 3 : CONDENSATION OF P-IODO-N-PHENYLNADIMIDE WITH 2,2-BIS-{4-(4-AMINOPHENOXY)PHENYL}PROPANE

A clean, dry 100 ml pressure vessel was charged with the following reagents under helium atmosphere in a dry box:

| | | |
|---|---|---|
| 2,2-bis-{4-(4-aminophenoxy)phenyl}propane | 0.616 g | 1.5 mmole |
| p-iodo-N-phenylnadimide | 1.096 g | 3.0 mmole |
| bis(triphenylphosphine)palladium(II) chloride | 0.03 g | 0.04 mmole |
| N,N-dimethylacetamide | 16 g | |
| 1,8-diazabicyclo[5.4.0]undec-7-ene (OBU) | 0.55 g | 3.61 mmole |

The vessel was charged with the reagents in the order listed, sealed and removed from the dry box. The vessel was purged three times with high purity carbon monoxide, pressurized to about 8 Kg/cm$^2$ with carbon monoxide and heated with magnetic stirring in an oil bath at 100° C. The reaction was continued 120 minutes, the vessel was removed from the oil bath, depressurized and opened. The reaction solution was diluted with 15 ml N,N-dimethylacetamide, filtered and precipitated into a stirred vessel containing 6:1 methanol:water. The product was collected by suction filtration and dried at 60° C. under vacuum for 48 hours. The yield was 1.31 grams which was 93% of theory. The proposed structure was similar to that of Example 1 except for the divalent 2,2-bis-{4-(4-aminophenoxy)phenyl}propane in place of the divalent oxydianiline. The NMR spectrum was consistant with the proposed structure.

EXAMPLE 4: CONDENSATION OF P-BROMO-N-PHENYLNADIMIDE WITH 3,4-OXYDIANILINE

The bromonadimide was prepared from p-bromoaniline following the same procedure outlined above for iodomaleimide.

The procedure outlined in Example 3 was repeated using the following reagents:

| | | | |
|---|---|---|---|
| p-bromophenyl nadimide | = | 0.955 g, | 3 mmoles |
| 3,4-oxydianiline | = | 0.30 g, | 1.5 mmole |
| dimethyl acetamide | = | 14 g | |
| DBU | = | 0.55 g | |
| palladium catalyst | = | 0.03 g | |

| | | |
|---|---|---|
| triphenylphosphine | = | 0.06 g |

The vessel was pressurized to slightly above 1 atmosphere with CO and heated at 100° C. for 2 hours. The reacting vessel was opened, the solution was filtered to remove the catalyst, and precipitated into methanol. The product was recrystallized from acetone and dried at 40° C. under high vacuum. Yield=0.33 g, 30% theory. NMR spectrum was consistent with the proposed structure.

The invention has been described in detail with particular reference to preferred embodiments thereof, but it will be understood that variations and modifications can be effected within the spirit and scope of the invention.

What is claimed is:

1. A method for the production of an arylamide bisnadimide, said method comprising the step of:
   condensing a nadimide compound having the nitrogen of said nadimide substituted with a halogen substituted aromatic group, with a primary diamine dinucleophile in the presence of carbon monoxide, a base and a palladium catalyst.

2. A method according to claim 1 wherein said nadimide is N-(4-iodophenylnadimide).

3. A method according to claim 1 wherein said primary diamine has the formula H$_2$NRNH$_2$ wherein R contains at least one aromatic group.

4. A method according to claim 3 wherein R is selected from the group consisting of

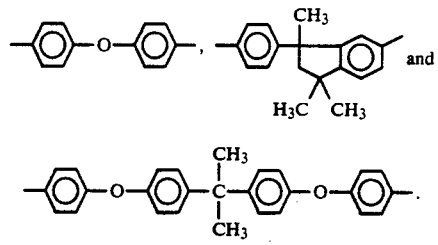

5. A method according to claim 1 wherein said process is carried out in the presence of a liquid reaction medium comprising a dipolar aprotic solvent.

6. A method according to claim 5 wherein said dipolar aprotic solvent is N,N-dimethylacetamide.

7. A method according to claim 1 wherein said palladium catalyst is bis(triphenylphosphine)palladium(II) chloride.

8. A method according to claim 1 wherein said method is carried out in the presence of an activation ligand.

9. A method according to claim 1 wherein said base is a tertiary amine.

10. A method according to claim 9 wherein said tertiary amine base is 1,8-diazabicyclo[5.4.0]undec-7-ene.

* * * * *